(12) United States Patent
Ginoux

(10) Patent No.: US 9,185,859 B2
(45) Date of Patent: Nov. 17, 2015

(54) MELON VARIETY NUN 26191 MEM

(71) Applicant: Nunhems B.V., Nunhem (NL)

(72) Inventor: Jean Paul Ginoux, Arles (FR)

(73) Assignee: Nunhems B.V., AC Nunhem (NL)

( * ) Notice: Subject to any disclaimer, the term of this patent is extended or adjusted under 35 U.S.C. 154(b) by 49 days.

(21) Appl. No.: 14/079,070

(22) Filed: Nov. 13, 2013

(65) Prior Publication Data

US 2014/0109252 A1     Apr. 17, 2014

(51) Int. Cl.
*A01H 5/08* (2006.01)
*C12N 15/82* (2006.01)
*A01G 1/00* (2006.01)

(52) U.S. Cl.
CPC .................. *A01H 5/08* (2013.01); *A01G 1/001* (2013.01)*C12N 15/8245* (2013.01); *C12N 15/8251*; (2013.01); *C12N 15/8274* (2013.01); *C12N 15/8279* (2013.01); *C12N 15/8286* (2013.01); *C12N 15/8289* (2013.01)

(58) Field of Classification Search
None
See application file for complete search history.

(56) References Cited

U.S. PATENT DOCUMENTS 8,987,561 B2 * 3/2015 Collin et al. .................. 800/309

* cited by examiner

*Primary Examiner* — Brent T Page

(57) ABSTRACT

The invention relates to the field of *Cucumis melo*, in particular to a new variety of *Cucumis melo reticulatus* designated NUN 26191 MEM, plants, seeds and melon fruit.

17 Claims, 1 Drawing Sheet

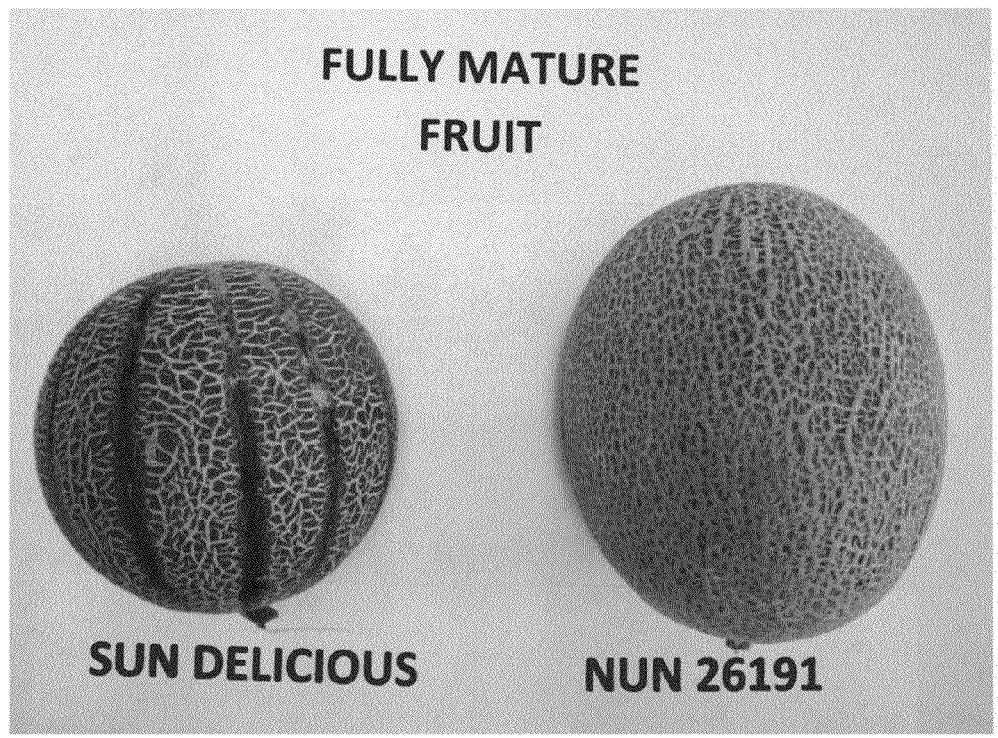

MELON VARIETY NUN 26191 MEM

FIELD OF THE INVENTION

The present invention relates to the field of plant breeding. In particular, a new and distinct hybrid variety of melon is provided, designated NUN 26191 MEM (or NUN 26191).

The new variety is a Common or Summer type (*Cucumis melo reticulatus*) with an yellow and gold colored rind at edible maturity.

Provided are seeds of NUN 26191 MEM, plants and plant parts produced from these seeds such as harvested fruit or parts thereof, pollen, cells, leaves or parts thereof, petioles, shoots or parts thereof, stems or parts thereof, roots or parts thereof, cuttings or parts thereof, flowers, vegetative reproductions of the variety NUN 26191 MEM, and progeny of the variety.

Melons or 'muskmelons', *Cucumis melo*, can be classified into: *C. melo cantalupensis, C. melo inodorous* and *C. melo reticulatus*.

*C. melo cantalupensis* are also referred to as Cantaloupes and are primarily round in shape with prominent ribs and almost no netting. Most have orange, sweet flesh and they are usually very fragrant. In contrast to the European cantaloupe, the North American 'Cantaloupe' is not of this type, but belongs to the true muskmelons.

*C. melo reticulatus* is the true muskmelon, with reticulated skin (netted) and includes Galia melons, Sharlyn melons and the North American cantaloupe. It is also known as "rockmelon" or as "Common" or "Summer" type melon.

*C. melo inodorous* (or winter melons) can be subdivided into different types, such as Honeydew melon, Piel de Sapo, Sugar melon, Japanese melon, etc.

Melons come in many sizes and shapes including round, oval, and cylindrical. The flesh is generally orange and quite sweet, but some varieties of melon and specifically, the Persian melons, can have green or white flesh. Some green-fleshed melons are quite sweet, but most of the green- and white-fleshed melons have a less sweet, but very refreshing flavor.

Winter melons, (*C. melo inodorus*), have a hard rind which preserves freshness, include the well-known casaba, crenshaw and honeydew types. They are usually quite large with smooth or netted rinds and can be deep green, bright yellow, beige and many shades in between. They come in just about any shape imaginable. The flesh can be green, white, pale yellow or orange and is usually incredibly sweet, but not very fragrant.

Honeydew melons are round to slightly oval shape and fruits at maturity of at least 1 kg (on average) or more. The flesh is usually pale green in color, while the smooth peel ranges from greenish to yellow. This fruit grows best in semi-arid climates and is harvested based on maturity. Maturity can be hard to judge, but is based upon ground color ranging from greenish white to creamy yellow. Quality is also determined by the honeydew having a surface free of scars or defects. Also, a honeydew should feel heavy for its size and have a waxy surface.

Sprite melon is a kind of melon, similar to honeydew, which originates from Japan. Since the late 1990s, it has been cultivated in North Carolina as a specialty crop and has increased in popularity in recent years. A sprite melon has a round shape and is typically about the size of a grapefruit (less than 700 g on average). The flesh of a sprite melon is ivory in color and firm, while the peel ranges from ivory (unripe) to yellowish (ripe). As the melon reaches optimal ripeness, horizontal brown markings will appear near the stem. The firm, juicy, sweet flesh of the sprite melon is usually eaten for dessert and tends to resemble the flavor of both pears and honeydew, however it is much sweeter than either of these and can often consist of 18% sugar.

The use of a type of melon is depending on a customer's preference for taste, color and aroma of the melon flesh. There is thus a need for a magenta fleshed Summer type of melon with unique rind color, absence of ribs, and excellent shipping qualities.

SUMMARY OF THE INVENTION

In one aspect of the invention, a seed of melon variety NUN 26191 MEM is provided, wherein a representative sample of said seed has been deposited under Accession Number NCIMB 42420.

In another aspect the invention provides for a hybrid variety of *Cucumis melo* reticulatus called NUN 26191 MEM. The invention also provides for a plurality of seeds of the new variety, plants produced from growing the seeds of the new variety NUN 26191 MEM, and progeny of any of these. Especially, progeny retaining one or more (or all) of the "distinguishing characteristics" or one or more (or all) of the "essential morphological and physiological characteristics" or essentially all physiological and morphological characteristics of NUN 26191 MEM referred to herein, are encompassed herein as well as methods for producing these.

In one aspect, such progeny have (essentially) all the physiological and morphological characteristics of melon variety NUN 26191 MEM when grown under the same environmental conditions.

Further, a melon fruit produced on a plant grown from these seeds is provided.

In yet another embodiment of the invention, an Essentially Derived Variety of NUN 26191 MEM having one, two or three physiological and/or morphological characteristics which are different from those of NUN 26191 MEM and which otherwise has all the physiological and morphological characteristics of NUN 26191 MEM, wherein a representative sample of seed of variety NUN 26191 MEM has been deposited under Accession Number NCIMB 42420, is provided.

Further, a vegetatively propagated plant of variety NUN 26191 MEM, or a part thereof, is provided having all the morphological and physiological characteristics of NUN 26191 MEM when grown under the same environmental conditions.

Also a plant part derived from variety NUN 26191 MEM is provided, wherein said plant part is selected from the group consisting of: harvested fruits or parts thereof, pollen, ovules, cells, leaves or parts thereof, petioles, shoots or parts thereof, stems or parts thereof, roots or parts thereof, cuttings, seeds, hypocotyl, cotyledon, flowers or parts thereof.

DEFINITIONS

"Melon" or "muskmelon" refers herein to plants of the species *Cucumis melo*. "Cultivated melon" refers to plants of *Cucumis melo* i.e. varieties, breeding lines or cultivars of the species *C. melo*, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species.

"Common" type or "Summer" type melon refers to melons of the *C. melo* reticulatus type.

"Netted" skin or rind refers to the presence of reticulate markings called 'netting' on the skin.

As used herein, the term "plant" includes the whole plant or any parts such as plant organs, plant cells, plant protoplasts, plant cell cultures or tissue cultures from which whole plants can be regenerated, plant callus, plant cell clumps, plant transplants, seedlings, plant cells that are intact in plants, plant clones or micropropagations, or parts of plants (e.g., harvested tissues, fruits or organs), such as plant cuttings, vegetative propagations, embryos, pollen, ovules, flowers, leaves, fruits, fruit flesh, seeds, clonally propagated plants, roots, stems, stalks, root tips, grafts, parts of any of these and the like, or derivatives thereof, preferably having the same genetic make-up (or very similar genetic make-up) as the plant from which it is obtained. Also any developmental stage is included, such as seedlings, cuttings prior or after rooting, mature and/or immature plants or mature and/or immature leaves.

"Tissue culture" refers to a composition comprising isolated cells of the same or a different type or a collection of such cells organized into parts of a plant. Tissue culture of various tissues of cucumber and regeneration of plants therefrom is well known and widely published (see, e.g., Sang-Gu et al. (1988), Plant Cell, Tissue and Organ Culture 12: 67-74; Colijn-Hooymans (1994), Plant Cell, Tissue and Organ Culture 39: 211-217). Similarly, the skilled person is well-aware how to prepare a "cell culture".

"UPOV descriptors" are the plant variety descriptors described for Muskmelon in the "Guidelines for the Conduct of Tests for Distinctness, Uniformity and Stability, TG/184/3 (Geneva 2001), as published by UPOV (International Union for the Protection of New Varieties and Plants, available on the world wide web at upov.int) and which can be downloaded from the world wide web at www.upov.int/en/publications/tg-rom/tg104/tg_104_5.pdf and is herein incorporated by reference in its entirety.

"USDA descriptors" are the plant variety descriptors for muskmelon/Cantaloupe (*Cucumis melo L.*) as published by the US Department of Agriculture, Agricultural Marketing Service, Science and Technology, Plant Variety Protection Office, Beltsville, MD 20705 (available on the world wide web at www.ams.usda.gov/AMSv1.0/) and which can be downloaded from the world wide web at http://www.ams.usda.gov/AMSv1.0/getfile?dDocName=STELDEV3003780.

"RHS" refers to the Royal Horticultural Society of England which publishes an official botanical color chart quantitatively identifying colors according to a defined numbering system, The chart may be purchased from Royal Horticulture Society Enterprise Ltd RHS Garden; Wisley, Woking; Surrey GU236QB, UK, e.g., the RHS colour chart: 2007 (The Royal Horticultural Society, charity No: 222879, PO Box 313 London SW1P2PE; sold by, e.g., TORSO-VERLAG, Obere Grüben 8. D-97877 Wertheim, Article-No.: Art62-00008 EAN-Nr.: 4250193402112). As used herein, the term "plant" includes the whole plant or any parts or derivatives thereof, preferably having the same genetic makeup as the plant from which it is obtained, such as plant organs (e.g. harvested or non-harvested fruits), plant cells, plant protoplasts, plant cell tissue cultures from which whole plants can be regenerated, plant calli, plant cell clumps, plant transplants, seedlings, hypocotyl, cotyledon, plant cells that are intact in plants, plant clones or micropropagations, or parts of plants (e.g. harvested tissues or organs), such as plant cuttings, vegetative propagations, embryos, pollen, ovules, fruits, flowers, leaves, seeds, clonally propagated plants, roots, stems, root tips, grafts, parts of any of these and the like. Also any developmental stage is included, such as seedlings, cuttings prior or after rooting, mature plants or leaves.

"Harvested plant material" refers herein to plant parts (e.g. fruits detached from the whole plant) which have been collected for further storage and/or further use.

"Harvested seeds" refers to seeds harvested from a line or variety, e.g. produced after self-fertilization or cross-fertilization and collected.

A plant having "(essentially) all the physiological and morphological characteristics" means a plant having the physiological and morphological characteristics when grown under the same environmental conditions of the plant from which it was derived, e.g. the progenitor plant, the parent, the recurrent parent, the plant used for tissue- or cell culture, etc. In certain embodiments the plant has all the physiological and morphological characteristics, except for certain characteristics mentioned, e.g. the characteristic(s) derived from a converted or introduced gene or trait and/or except for the characteristics which differ in an EDV. A plant have one or more "essential physiological and/or morphological characteristics" or one or more "distinguishing characteristics" refers to a plant having (or retaining) one or more of the characteristics mentioned in Table 1 when grown under the same environmental conditions that distinguish NUN 26191 MEM from the most similar varieties (such as variety Sun Delicious), such as but not limited to rind color at edible maturity, lobes of mature blade of third leaf, length of seed cavity, width of seed cavity.

The physiological and/or morphological characteristics mentioned above are commonly evaluated at significance levels of 1%, 5% or 10% significance level, when measured under the same environmental conditions. For example, a progeny plant of NUN 26191 MEM may have one or more (or all) of the essential physiological and/or morphological characteristics of NUN 96141 ME listed in Table 1, as determined at the 5% significance level when grown under the same environmental conditions.

As used herein, the term "variety" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

A variety is referred to as an "Essentially Derived Variety" (EDV) i.e., shall be deemed to be essentially derived from another variety, "the initial variety" when (i) it is predominantly derived from the initial variety, or from a variety that is itself predominantly derived from the initial variety, while retaining the expression of the essential characteristics that result from the genotype or combination of genotypes of the initial variety; (ii) it is clearly distinguishable from the initial variety; and (iii) except for the differences which result from the act of derivation, it conforms to the initial variety in the expression of the essential characteristics that result from the genotype or combination of genotypes of the initial variety. Thus, an EDV may be obtained for example by the selection of a natural or induced mutant, or of a somaclonal variant, the selection of a variant individual from plants of the initial variety, backcrossing, or transformation by genetic engineering.

"Plant line" is for example a breeding line which can be used to develop one or more varieties.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) leaf, pollen, embryo, cotyledon, hypocotyl, cells, protoplasts, meristematic cell, root, root tip, pistil, anther, flower, shoot tip, shoot, stem, fruit, petiole, etc. When a whole plant is regenerated by vegetative propagation, it is also referred to as a vegetative propagation.

"Selfing" refers to self-pollination of a plant, i.e., the transfer of pollen from the anther to the stigma of the same plant. "Crossing" refers to the mating of two parent plants.

"Average" refers herein to the arithmetic mean.

"Locus" (plural loci) refers to the specific location of a gene or DNA sequence on a chromosome. A locus may confer a specific trait.

"Allele" refers to one or more alternative forms of a gene locus. All of these loci relate to one trait. Sometimes, different alleles can result in different observable phenotypic traits, such as different pigmentation. However, many variations at the genetic level result in little or no observable variation. If a multicellular organism has two sets of chromosomes, i.e. diploid, these chromosomes are referred to as homologous chromosomes. Diploid organisms have one copy of each gene (and therefore one allele) on each chromosome. If both alleles are the same, they are homozygotes. If the alleles are different, they are heterozygotes.

"Genotype" refers to the genetic composition of a cell or organism.

"Maturity" refers to the fruit developmental stage when the fruit has fully developed (reached its final size), begins to ripen and undergoes ripening, during which fruits can be divided into 1, 2, 3 or more maturity stages. Thereafter, fruits become overripe. In particular embodiments "maturity" is defined as the mature stage of fruit development and optimal time for harvest. In one embodiment a "mature" melon is defined as having reached the stage of maturity which will insure the proper completion of the normal ripening process. In particular embodiments, fruit should be harvested at a maturity stage i.e. substantially near maximum sweetness and flavor intensity.

"Harvest maturity" is referred to as the stage at which a melon fruit is ripe or ready for harvest or the optimal time to harvest the fruit. In one embodiment, harvest maturity is the stage which allows proper completion of the normal ripening.

"Abscission zone" is the layer or zone separating the fruit from the peduncle.

"Cavity" or "seed cavity" is the center of the fruit containing the maternal tissues and seeds.

"Flavor" refers to the sensory impression of a food or other substance, especially a melon fruit or fruit part (fruit flesh) and is determined mainly by the chemical senses of taste and smell. Flavor is influenced by texture properties and by volatile and/or non-volatile chemical components (organic acids, lipids, carbohydrates, etc.).

"Aroma" refers to smell (or odor) characteristics of melon fruits or fruit parts (fruit flesh).

The term "traditional breeding techniques" encompasses herein crossing, selfing, selection, double haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one melon line or variety to another.

"Backcrossing" is a traditional breeding technique used to introduce a trait into a plant line or variety. The plant containing the trait is called the donor plant and the plant into which the trait is transferred is called the recurrent parent. An intial cross is made between the donor parent and the recurrent parent to produce progeny plants. Progeny plants which have the trait are then crossed to the recurrent parent. After several generations of backcrossing and/or selfing the recurrent parent comprises the trait of the donor. The plant generated in this way may be referred to as a "single trait converted plant".

"Progeny" as used herein refers to plants derived from a plant designated NUN 26191 MEM. Progeny may be derived by regeneration of cell culture or tissue culture or parts of a plant designated NUN 26191 MEM or selfing of a plant designated NUN 26191 MEM or by producing seeds of a plant designated NUN 26191 MEM. In further embodiments, progeny may also encompass plants derived from crossing of at least one plant designated NUN 26191 MEM with another melon plant of the same or another variety or (breeding) line, or wild melon plants, backcrossing, inserting of a locus into a plant or mutation. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above.

The terms "gene converted" or "conversion plant" in this context refer to melon plants which are developed by backcrossing wherein essentially all of the desired morphological and physiological characteristics of parent are recovered in addition to the one or more genes transferred into the parent via the backcrossing technique or via genetic engineering. Likewise a "Single Locus Converted (Conversion) Plant" refers to plants which are developed by plant breeding techniques comprising or consisting of backcrossing, wherein essentially all of the desired morphological and physiological characteristics of a melon variety are recovered in addition to the characteristics of the single locus having been transferred into the variety via the backcrossing technique and/or by genetic transformation.

"Transgene" or "chimeric gene" refers to a genetic locus comprising a DNA sequence which has been introduced into the genome of a melon plant by transformation. A plant comprising a transgene stably integrated into its genome is referred to as "transgenic plant".

The term "mean" refers to the arithmetic mean of several measurements. The skilled person understands that the appearance of a plant depends to some extent on the growing conditions of said plant. Thus, the skilled person will know typical growing conditions for Summer melons described herein. The mean, if not indicated otherwise within this application, refers to the arithmetic mean of measurements on at least 10 different, randomly selected plants of a variety or line.

DRAWINGS

The drawings described herein are for illustration purposes only and are not intended to limit the scope of the present teachings in any way.

FIG. 1 shows the absence of ribs in NUN 26191 MEM fruits and the presence of ribs in Sun Delicious fruits.

DETAILED DESCRIPTION

A *C. melo reticulatus* is a true muskmelon and includes Galia melons, Sharlyn melons and the North American cantaloupe. A number of characteristics are important to melon breeders such as (a) the fruit length; (b) the fruit diameter; (c) the fruit weight; (d) the fruit brix; (e) rind thickness and (f) time point of harvest.

The present invention relates to a *Cucumis melo reticulatus* melon type, referred to as NUN 26191 MEM which has an yellow and gold colored rind at edible maturity (most similar to Sun Delicious, a commercial variety of Nunhems B.V.) or progeny or EDVs thereof.

Thus, the melon plant of the invention with its yellow and gold colored rind when fruits are at edible maturity differs from the most similar comparison variety Sun Delicious type melons—which rind color becomes gold and orange when the fruits reach the state of edible maturity—in one or more characteristics (referred herein to as "distinguishing characteristics" or "distinguishing morphological and/or physiological characteristics" (or essential physiological and/or morphological characteristics) selected from: 1) NUN 26191 MEM has magenta colored flesh, e.g. RHS Orange Red 32D near the cavity, RHS Orange Red 32C in the center and RHS 32C near the rind, whereas Sun Delicious has orange colored flesh, e.g. RHS Orange 24B near the cavity, RHS Orange 24A in the center and RHS 24A near the rind; 2) NUN 26191 MEM has a weight of fruit (at edible maturity) that is at least about 15%, or preferably 16%, 17%, 18%, 19%, 20%, or even about 20.9% bigger than the weight of Sun Delicious; 3) NUN 26191 MEM has a thickness at medial of the rind that is at least about 15%, or preferably 16%, 17%, 18%, 19%, 20%, 21%, or even about 21.8% bigger than the thickness at medial of Sun Delicious; 4) NUN 26191 MEM has an absence of ribs, whereas Sun Delicious has a presence of ribs; 5) NUN 26191 MEM has excellent shipping quality, whereas Sun Delicious has fair shipping quality.

It is understood that "significant" differences refer to statistically significant differences, when comparing the characteristic between two plant lines or varieties when grown under the same conditions. Preferably at least about 10, 15, 20 or more plants per line or variety are grown under the same conditions and characteristics are measured on at least about 10, 15, 20 or more randomly selected plant or plant parts to obtain averages. Thus, physiological and morphological characteristics or traits are commonly evaluated at a significance level of 1%, 5% or 10%, when measured in plants grown under the same environmental conditions.

Thus, in one aspect, the invention provides seeds of the melon variety designated NUN 26191 MEM wherein a representative sample of seeds of said variety was deposited under the Budapest Treaty, with Accession number NCIMB 42420.

Seeds of NUN 26191 MEM are obtainable by crossing the male parent with the female parent and harvesting the seeds produced on the female parent. The resultant NUN 26191 MEM seeds can be grown to produce NUN 26191 MEM plants. In one embodiment a plurality of NUN 26191 MEM seeds are packaged into small and/or large containers (e.g., bags, cartons, cans, etc.). The seeds may be treated with various compounds, such as seed coatings or fungicides or insecticides.

Also provided are plants of melon variety NUN 26191 MEM, or a fruit or other plant part thereof, produced from seeds, wherein a representative sample of said seeds has been deposited under the Budapest Treaty, with Accession Number NCIMB 42420. Also included is a cell culture or tissue culture produced from such a plant or a plant regenerated from such a cell or tissue culture said plant expressing all the morphological and physiological characteristics of NUN 26191 MEM.

Plants of NUN 26191 MEM can be produced by seeding directly in the ground (e.g., field) or by germinating the seeds in controlled environment conditions (e.g., greenhouses) and then transplanting the seedlings into the field. For example by sowing the seed into prepared seed beds where they will remain for the entire production of the crop. Alternatively, the melon seed may be planted through a black plastic mulch. The dark plastic will absorb heat from the sun, warming the soil early. It will also help to conserve moisture during the growing season, controls weeds and makes harvesting easier and cleaner. See for example www.anrcatalog.ucdavis.edu for cultivation, harvesting, handling and postharvest methods commonly used.

In another aspect, the invention provides for a melon plant of melon variety NUN 26191 MEM, a representative sample of seed from said variety has been deposited under the Budapest Treaty, with Accession number NCIMB 42420.

In other aspects, the invention provides for a fruit of melon variety NUN 26191 MEM, or a plant part, such as pollen, flowers, shoots or cuttings of variety NUN 26191 MEM or parts thereof.

In still another aspect the invention provides a method of producing a melon plant, comprising crossing a plant of melon variety NUN 26191 MEM with a second melon plant one or more times, and selecting progeny from said crossing.

In yet another aspect the invention provides a method of producing a melon plant, comprising selfing a plant of melon variety NUN 26191 MEM one or more times, and selecting progeny from said selfing.

In other aspects, the invention provides for progeny of variety NUN 26191 MEM such as progeny obtained by further breeding NUN 26191 MEM. Further breeding NUN 26191 MEM includes selfing NUN 26191 MEM one or more times and/or cross-pollinating NUN 26191 MEM with another melon plant or variety one or more times. In particular, the invention provides for progeny that retain all the essential morphological and physiological characteristics of NUN 26191 MEM or that retain one or more of the distinguishing characteristics of the melon type described further above and when grown under the same environmental conditions. In another aspect, the invention provides for vegetative reproductions of the variety and essentially derived varieties (EDVs) of NUN 26191 MEM.

The morphological and/or physiological differences between plants according to the invention, i.e. NUN 26191 MEM or progeny thereof, or an EDV thereof, and other known varieties can easily be established by growing NUN 26191 MEM next to the other varieties (in the same field, under the same environmental conditions), preferably in several locations which are suitable for said melon cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18'807", USA, whereby e.g. type of melon, area of best adaption in USA, days from seeding to harvest, plant fertility, plant habit, leaf shape, leaf lobes, leaf color, leaf length, width and surface, fruit length, fruit diameter, fruit weight, fruit shape, fruit surface, blossom scar, rib presence and number of ribs per fruit, rib width, rib surface, suture depth, suture surface, shipping quality, fruit abscission, rind net presence/distribution/coarseness/interlacing/interstices, rind texture, rind texture thickness, rind color at edible maturity, mottling color, net color, furrow (suture), rind color at full maturity, mottling color, net color, furrow (suture), flesh color near cavity, flesh color in center, flesh color near rind, % soluble solids, flesh aroma, flesh flavor, seed cavity length, seed cavity width, seed cavity shape, number of seeds per fruit, weight per 1,000 seeds, disease resistances and/or insect resistances can be measured and directly compared.

Morphological and physiological characteristics (and distinguishing characteristics) of NUN 26191 MEM, are provided in the Examples, in Table 1. Encompassed herein are also plants derivable from NUN 26191 MEM (e.g. by selfings and/or crossing and/or backcrossing with NUN 26191 MEM and/or progeny thereof) comprising all the physiological and morphological characteristics of NUN 96141 listed in Table 1 as determined at the 5% significance level when grown under the same environmental conditions and/or comprising one or more (or all; or all except one, two or three) of the distinguishing characteristics as determined at the 5% significance level when grown under the same environmental conditions.

Also at-harvest and/or post-harvest characteristics of fruits can be compared, such as cold storage holding quality (browning), post-harvest rind firmness and/or flesh firmness, and juiciness can be measured using known methods. Melon fruits of NUN 26191 MEM or progeny thereof remaining essentially free of external blemishes and having good eating quality.

Flesh firmness can for example be measured using a penetrometer, e.g. by inserting a probe into the fruit flesh and determining the insertion force, or other methods.

The morphological and/or physiological characteristics may vary somewhat with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the Royal Horticultural Society Chart (http://www.rhs.org.uk/Plants/RHS-Publications/RHS-colour-charts).

In a preferred embodiment, the invention provides for melon fruits of variety NUN 26191 MEM, or a part of the fruit. In another embodiment, the invention provides for a container comprising or consisting of a plurality of harvested melon fruits of NUN 26191 MEM, or progeny thereof, or a derived variety, such as an EDV.

In yet a further embodiment, the invention provides for a method of producing a new melon plant. The method comprises crossing a plant of the invention NUN 26191 MEM, or an EDV thereof, or a progeny plant thereof, either as male or as female parent, with a second melon plant (or a wild relative of melon) one or more times, and/or selfing a melon plant according to the invention i.e. NUN 26191 MEM, or an EDV thereof, or a progeny plant thereof, one or more times, and selecting progeny from said crossing and/or selfing. The second melon plant may for example be a line or variety of the species *C. melo cantalupensis, C. melo inodorous* or *C. melo reticulatus*.

Progeny are either the generation (seeds) produced from the first cross (F1) or selfing (S1), or any further generation produced by crossing and/or selfing (F2, F3, etc.) and/or backcrossing (BC1, BC2, etc.) one or more selected plants of the F1 and/or S1 and/or BC1 generation (or plants of any further generation, e.g. the F2) with another melon plant (and/or with a wild relative of melon). Progeny may have all the physiological and morphological characteristics of melon variety NUN 26191 MEM when grown under the same environmental conditions and/or progeny may have (be selected for having) one or more of the distinguishing characteristics of melons of the invention. Using common breeding methods such as backcrossing or recurrent selection, one or more specific characteristics may be introduced into NUN 26191 MEM, to provide an EDV of NUN 26191 MEM.

The invention provides for methods of producing varieties which retain all the morphological and physiological characteristics of NUN 26191 MEM. The invention provides also for methods of producing EDVs (Essentially Derived Varieties) of NUN 26191 MEM which differ from NUN 26191 MEM in one, two, three or more morphological and/or physiological characteristics, but which are still genetically closely related to NUN 26191 MEM. The relatedness can, for example be determined by fingerprinting techniques (e.g., making use of isozyme markers and/or molecular markers such as SNP markers, AFLP markers, microsatellites, minisatellites, RAPD markers, RFLP markers and others). A plant is "closely related" to NUN 26191 MEM if its DNA fingerprint is at least 80%, 90%, 95% or 98% identical to the fingerprint of NUN 26191 MEM. In a preferred embodiment AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (Pisanu et al. ISHS 2004, Acta Hort. 660). The invention also provides plants and varieties obtained by these methods. EDVs may be produced by crossing and/or selfing, or alternatively, an EDV may simply be identified and selected amongst NUN 26191 MEM plants, or progeny thereof, e.g. by identifying a variant within NUN 26191 MEM or progeny thereof (e.g. produced by selfing) which variant differs from NUN 26191 MEM in one, two or three of the morphological and/or physiological characteristics (e.g. in one, two or three distinguishing characteristics), e.g. those listed in Table 1 or others.

By crossing and/or selfing also (one or more) single traits may be introduced into the variety of the invention i.e. NUN 26191 MEM (e.g., using backcrossing breeding schemes), while retaining the remaining morphological and physiological characteristics of NUN 26191 MEM and/or while retaining one or more distinguishing characteristics. A single trait converted plant may thereby be produced. For example, disease resistance genes may be introduced, genes responsible for one or more quality traits, yield, etc. Both single genes (dominant or recessive) and one or more QTLs (quantitative trait loci) may be transferred into NUN 26191 MEM by breeding with NUN 26191 MEM.

Any pest or disease resistance genes may be introduced into a plant according to the invention, i.e. NUN 26191 MEM, progeny thereof or into an EDV of NUN 26191 MEM. Resistance to one or more of the following diseases is preferably introduced into plants of the invention: Bacterial Wilt, Root Rot, Crown Blight, Melon Rust, Powdery Mildew, Verticillum Wilt, Sulphur Burn, Scab, Watermelon Mosaic, Downy Mildew, Fusarium oxysporum f.sp. melonis (Fom) race 0, Fusarium oxysporum f.sp. melonis (Fom) race 1, Fusarium oxysporum f.sp. melonis (Fom) race 2, Fusarium oxysporum f.sp. melonis (Fom) race 1-2, Fusarium Wilt R2, Root Knot (Nematode), Anthracnose, Cucumber Mosiac, and Squash Mosaic.

Resistance to one or more of the following pests is preferably present or introduced into plants of the invention: Aphid resistance, Pickle Worm, Darkling Ground Beetle, Banded Cucumber Beetle, Mite, Western Spotted Cucumber Beetle, Melon Leafhopper, Melon Worm, Western Striped Cucumber Beetle or Melon Leafminer. Other resistance genes, against pathogenic viruses, fungi, bacteria or pests may also be introduced.

Thus, invention also provides a method for developing a melon plant in a melon breeding program, using a melon plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 26191 MEM or progeny thereof, or an EDV thereof, with a different melon plant, and wherein one or more offspring of the crossing are subject to one or more plant breeding techniques selected from the group consisting of recurrent selection, backcrossing, pedigree breeding, mass selection, mutation breeding and genetic marker enhanced selection (see e.g. Martin et al. 2008, Australian Journal of Crop Science 1(2): 43-46). For breeding methods in general see Principles of Plant Genetics and Breeding, 2007, George Acquaah, Blackwell Publishing, ISBN-13: 978-1-4051-3646-4.

The invention thus also provides a method of introducing a single locus conversion, or single trait conversion, into a melon plant according to the invention and/or into NUN 26191 MEM comprising:
(a) crossing a melon plant of variety NUN 26191 MEM, a representative sample of seed of said variety having been deposited under Accession Number NCIMB 42420, with a second melon plant comprising a desired single locus to produce F1 progeny plants;
(b) selecting F1 progeny plants that have the single locus to produce selected F1 progeny plants;
(c) crossing the selected progeny plants with a plant of NUN 26191 MEM, to produce backcross progeny plants;
(d) selecting backcross progeny plants that have the single locus and one or more (or all) distinguishing characteristics of melons according to the invention and/or all the physiological and morphological characteristics of NUN 26191 MEM to produce selected backcross progeny plants; and
(e) optionally repeating steps (c) and (d) one or more times in succession to produce selected second, third or fourth or higher backcross progeny plants that comprise the single locus and otherwise one or more (or all) the distinguishing characteristics of the melons according to the invention and/or comprise all of the physiological and morphological characteristics of NUN 26191 MEM, when grown in the same environmental conditions.

The above method is provided, wherein the single locus confers a trait, wherein the trait is pest resistance or disease resistance.

In one embodiment the trait is disease resistance and the resistance is conferred to Bacterial Wilt, Root Rot, Crown Blight, Melon Rust, Powdery Mildew, Verticillum Wilt, Sulphur Burn, Scab, Watermelon Mosaic, Downy Mildew, *Fusarium oxysporum f.sp. melonis* (Fom) race 0, *Fusarium oxysporum f.sp. melonis* (Fom) race 1, *Fusarium oxysporum f.sp. melonis* (Fom) race 2, *Fusarium oxysporum f.sp. melonis* (Fom) race 1-2, *Fusarium* Wilt R2, Root Knot (Nematode), Anthracnose, Cucumber Mosiac, or Squash Mosaic.

In one embodiment the trait is pest resistance and the resistance is conferred to Aphid, Pickle Worm, Darkling Ground Beetle, Banded Cucumber Beetle, Mite, Western Spotted Cucumber Beetle, Melon Leafhopper, Melon Worm, Western Striped Cucumber Beetle or Melon Leafminer.

The invention also provides a melon plant comprising at least a first set of the chromosomes of melon line NUN 26191 MEM, a sample of seed of said line having been deposited under Accession Number NCIMB 42420; further comprising a single locus conversion, wherein said plant has essentially all of the morphological and physiological characteristics of the plant comprising at least a first set of the chromosomes of melon line NUN 26191 MEM. In another embodiment, this single locus conversion confers a trait selected from the group consisting of male sterility, herbicide tolerance, insect resistance, pest resistance, disease resistance, environmental stress tolerance, modified carbohydrate metabolism and modified protein metabolism.

In one embodiment, NUN 26191 MEM may also be mutated (by e.g. irradiation, chemical mutagenesis, heat treatment, etc.) and mutated seeds or plants may be selected in order to change one or more characteristics of NUN 26191 MEM. Also natural mutants or natural variants of NUN 26191 MEM may be identified and used in breeding. Methods such as TILLING and/or EcoTILLING may be applied to melon populations in order to identify mutants. Similarly, NUN 26191 MEM may be transformed and regenerated, whereby one or more chimeric genes are introduced into the variety or into an EDV thereof. Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 26191 MEM, or progeny thereof, by transforming NUN 26191 MEM or progeny thereof with a transgene that confers the desired trait, wherein the transformed plant retains all the phenotypic and/or morphological and/or physiological characteristics of NUN 26191 MEM or the progeny thereof and contains the desired trait.

The invention also provides for progeny of melon variety NUN 26191 MEM obtained by further breeding with NUN 26191 MEM. In one aspect progeny are F1 progeny obtained by crossing NUN 26191 MEM with another plant or S1 progeny obtained by selfing NUN 26191 MEM. Also encompassed are F2 progeny obtained by selfing the F1 plants. "Further breeding" encompasses traditional breeding (e.g., selfing, crossing, backcrossing), marker assisted breeding, and/or mutation breeding. In one embodiment, the progeny have one or more (or all) of the distinguishing characteristics mentioned further above when grown under the same environmental conditions. In a further embodiment the progeny have all the physiological and morphological characteristics of variety NUN 26191 MEM when grown under the same environmental conditions. In another embodiment the progeny are EDVs and/or have one, two, or three distinct traits (qualitative or quantitative) introduced into NUN 26191 MEM, while retaining all the other physiological and morphological characteristics of variety NUN 26191 MEM when grown under the same environmental conditions.

An EDV is an Essentially Derived Variety of NUN 26191 MEM having one, two or three physiological and/or morphological characteristics which are different from those of NUN 26191 MEM and which otherwise has all the physiological and morphological characteristics of NUN 26191 MEM, wherein a representative sample of seed of variety NUN 26191 MEM has been deposited under Accession Number NCIMB 42420. In particular variants which differ from NUN 26191 MEM in one, two or three of the characteristics mentioned in Table 1 are encompassed.

In one aspect, the EDV differs from NUN 26191 MEM in one, two or three of the distinguishing morphological and/or physiological characteristics selected from the group consisting of: : I) flesh color at edible maturity, II) fruit weight at edible maturity, III) thickness at medial of the rind, IV) presence of ribs, and V) shipping quality.

In another embodiment the EDV may differ from NUN 26191 MEM in one, two or three morphological or physiological characteristic other than the "distinguishing morphological and/or physiological characteristics" (or essential physiological and/or morphological characteristics) of NUN 26191 MEM selected from: i) length of fruit (at edible maturity); 2) diameter of fruit (at edible maturity); 3) width of seed cavity; 4) number of seeds per fruit; 5) petiole length.

Melons according to the invention, such as the variety NUN 26191 MEM, or its progeny, or an EDV of NUN 26191 MEM, can also be reproduced using vegetative reproduction methods. Therefore, the invention provides for a method of producing plants, or a part thereof, of variety NUN 26191 MEM, comprising vegetative propagation of variety NUN 26191 MEM. Vegetative propagation comprises regenerating a whole plant from a part of variety NUN 26191 MEM (or from its progeny or from an EDV of NUN 26191 MEM), such as a cutting, a cell culture or a tissue culture.

The invention also provides for a vegetatively propagated plant of variety NUN 26191 MEM (or from its progeny or from an EDV of NUN 26191 MEM), or a part thereof, having one or more distinguishing characteristics and/or all the morphological and physiological characteristics of NUN 26191 MEM (except for the characteristics differing in the EDV), when grown under the same environmental conditions.

Parts of NUN 26191 MEM (or of its progeny or of an EDV of NUN 26191 MEM) encompass any cells, tissues, organs obtainable from the seedlings or plants, such as but not limited to: melon fruits or parts thereof, cuttings, hypocotyl, cotyledon, pollen and the like. Such parts can be stored and/or processed further. Encompassed are therefore also food or feed products comprising one or more of such parts, such as canned melon fruit from NUN 26191 MEM or from progeny thereof, or from a derived variety, such as an EDV.

In one aspect haploid plants and/or double haploid plants of NUN 26191 MEM, or an EDV or progeny of any of these, are encompassed herein. Haploid and double haploid (DH) plants can, for example, be produced by cell or tissue culture and chromosome doubling agents and regeneration into a whole plant. For DH production chromosome doubling may be induced using known methods, such as colchicine treatment or the like.

Also provided are plant parts derived from variety NUN 26191 MEM (or from its progeny or from an EDV of NUN 26191 MEM), or from a vegetatively propagated plant of NUN 26191 MEM (or from its progeny or from an EDV of NUN 26191 MEM), being selected from the group consisting of: harvested fruits or parts thereof, pollen, cells, leaves or parts thereof, petioles, cotyledons, hypocotyls, shoots or parts thereof, stems or parts thereof, roots or parts thereof, cuttings, or flowers.

In one embodiment, the invention provides for extracts of a plant described herein and compositions comprising or consisting of such extracts. In a preferred embodiment, the extract consists of or comprises tissue of a plant described herein or is obtained from such tissue.

In one aspect the invention relates to a *Cucumis melo* plant of the Common or Summer type which has 1) an excellent shipping quality; 2) an average fruit weight of about 1600 to about 2400 grams, preferably about 1800 to about 2200 grams, or about 1890 to about 2090 grams or even about 1970 to about 12010 grams; 3) no ribs; 4) Magenta fruit flesh; 5) an average number of seeds of about 564 to about 764, preferably between about 614 and about 714, or even between about 654 and 674.

The invention also provides for a food or feed product comprising or consisting of a plant part described herein preferably a melon fruit or part thereof and/or an extract from a plant part described herein. The food or feed product may be fresh or processed, e.g., canned, steamed, boiled, fried, blanched and/or frozen, etc.

For example, containers such as cans, boxes, crates, bags, cartons, Modified Atmosphere Packagings, films (e.g. biodegradable films), etc. comprising plant parts of plants (fresh and/or processed) described herein are also provided herein.

Marketable melon fruits are generally sorted by size and quality after harvest.

All documents (e.g., patent publications) are herein incorporated by reference in their entirety.

CITED REFERENCES

Acquaah, Principles of Plant Genetics and Breeding, 2007, Blackwell Publishing, ISBN-13: 978-1-4051-3646-4
Colijn-Hooymans (1994), Plant Cell, Tissue and Organ Culture 39: 211-217
http://www.ams.usda.gov/AMSv1.0/getfile?dDocName=STELDEV3003780
http://www.rhs.org.uk/Plants/RHS-Publications/RHS-colour-charts
http://www.upov.int/en/publications/tg-rom/tg104/tg_104_5.pdf
Martin et al. 2008, Australian Journal of Crop Science 1(2): 43-46
Pisanu et al. ISHS 2004, Acta Hort. 660
Sang-Gu et al. (1988), Plant Cell, Tissue and Organ Culture 12: 67-74
Vos et al. 1995, Nucleic Acid Research 23: 4407-4414

EXAMPLES

Development of NUN 26191 MEM

The hybrid NUN 26191 MEM was developed from a male and female proprietary inbred line of Nunhems. The female and male parents were crossed to produce hybrid (F1) seeds of NUN 26191 MEM. The seeds of NUN 26191 MEM can be grown to produce hybrid plants and parts thereof (e.g. melon fruit). The hybrid NUN 26191 MEM can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant concluded that NUN 26191 MEM is uniform and stable.

DEPOSIT INFORMATION

A total of 2500 seeds of the hybrid variety NUN 26191 MEM were deposited according to the Budapest Treaty by Nunhems B.V. on Jun. 17, 2015, at the NCIMB Ltd., Ferguson Building, Craibstone Estate, Bucksburn, Aberdeen AB21 9YA, United Kingdom (NCIMB). The deposit has been assigned Accession Number NCIMB 42420. A deposit of NUN 26191 MEM and of the male and female parent line is also maintained at Nunhems B.V. Access to the deposit will be available during the pendency of this application to persons determined by the Director of the U.S. Patent Office to be entitled thereto upon request. Subject to 37 C.F.R. §1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

"USDA descriptors" are plant variety descriptors described for melon in the "Objective Description of Variety Muskmelon/Cantaloupe (*Cucumis melo L.*)—Exhibit C" of the U.S. Department of Agriculture, Agricultural Marketing Service, Science and Technology, Plant Variety Protection Office, Beltsville, Md. 20705, which can be downloaded from http://www.ams.usda.gov/AMSv1.0/getfile?dDocName=STELDEV3003780, and is herein incorporated by reference in its entirety.

The most similar variety to NUN 26191 MEM is Sun Delicious a commercial variety from Nunhems. In Table 1 a comparison between NUN 26191 MEM and Sun Delicious is shown based on a trial in the USA. Trial location: Acampo Calif. USA, (coordinates: 38°19'2873"N, −121°23'2637"W), USA 2013. Average temperatures for the day were 33.1° C. and 14.7° C. for the night. Planting date: 9 May 2013, transplant date: 5 Jun. 2013, harvesting dates harvesting dates 98 days after sowing (NUN26191 MEM); 92 days after sowing (check variety Sun Delicious).( Two replication of 50 plants each, from which 15 plants or plant parts were randomly selected to measure characteristics. In Table 1 the USDA descriptors of NUN 26191 MEM (this application) and reference Sun Delicious (commercial variety).

TABLE 1

| USDA Descriptor | Application Variety NUN 26191 MEM | Comparison Variety Sun Delicious |
| --- | --- | --- |
| 1. TYPE: | 5 | 5 |
| 1 = Persian 2 = Honey Dew | | |
| 3 = Casaba 4 = Crenshaw | | |
| 5 = Common or Summer | | |
| 6 = Other _____ . | | |
| 2. AREA OF BEST ADAPTATION IN U.S.A.: | 3 | 3 |
| 1 = Southeast 2 = Northeast/North Central | | |
| 3 = Southwest | | |
| 4 = Most Areas | | |
| 3. MATURITY: | 98 | 92 |
| Days From Seeding to Harvest | | |
| 4. PLANT: | | |
| Fertility: | 1 | 1 |
| 1 = Andromonoecious 2 = Monoecious 3 = Gynoecious | | |
| 4 = Other _____ | | |
| Habit: | 1 | 1 |
| 1 = Vine 2 = Semi-bush 3 = Bush | | |
| 5. LEAF: | (Mature Blade of Third Leaf) | |
| Shape: | 3 | 3 |
| 1 = Orbicular 2 = Ovate 3 = Reniform (Cordate) | | |
| Lobes: | 2 | 2 |
| 1 = Not Lobed 2 = Shallowly Lobed 3 = Deeply Lobed | | |
| Color: | 2 | 2 |
| 1 = Light Green (Honey Dew) | | |
| 2 = Medium Green | | |
| 3 = Dark Green (Rio Gold) | | |
| Color Chart Name | RHS | RHS |
| Color Chart Code (GG = Green Group; YGG = Yellow Green Group) | Green N137A | Yellow Green 147A |
| Length mm | 112 | 113.4 |
| Width mm | 157.7 | 158.3 |
| Surface: | 3 | 3 |
| 1 = Pubescent 2 = Glabrous 3 = Scabrous | | |
| 6. FRUIT: | (at Edible Maturity): | |
| Length in cm | 16.9 | 15.6 |
| Diameter in cm | 14.6 | 14.0 |
| Weight in gram | 1989.7 | 1644.9 |
| Shape: 1 = Oblate 2 = Oval 3 = Round | 2 | 2 |
| 4 = Elongate-Cylindrical 5 = Spindle 6 = Acorn | | |
| Surface: 1 = Smooth 2 = Netted 3 = Corrugated 4 = Warted | 2 | 2 |
| Blossom Scar: | 1 | 1 |
| 1 = Obscure 2 = Conspicuous | | |
| Rib Presence: | 1 | 2 |
| 1 = Absent 2 = Present | | |
| No. Ribs per Fruit | NA | 9.5 |

TABLE 1-continued

| USDA Descriptor | Application Variety NUN 26191 MEM | Comparison Variety Sun Delicious |
|---|---|---|
| Rib Width at Medial in mm | N.A. | 43.24 |
| Ribs Surface: 1 = Smooth 2 = Netted | N.A. | 1 |
| Suture Depth: 1 = Shallow (Golden Delight) 2 = Medium 3 = Deep (Hackensack) | N.A. | 1 |
| Suture Surface: 1 = Smooth 2 = Netted | N.A. | 1 |
| Shipping Quality: 1 = Poor (Home Garden) 2 = Fair (Short Distance Shipping) 3 = Excellent (Long Distance Shipping) | 3 | 2 |
| Fruit Abscission: 1 = When Ripe 2 = When Overripe 3 = Do Not Abscise | 3 | 3 |
| 7. RIND NET: | | |
| Net Presence: 1 = Absent 2 = Sparse 3 = Abundant | 3 | 3 |
| Distribution: 1 = Spotty 2 = Covers Entire Fruit | 2 | 2 |
| Coarseness: 1 = Fine 2 = Medium Coarse 3 = Very Coarse | 2 | 2 |
| Interlacing: 1 = None 2 = Some 3 = Complete | 3 | 3 |
| Interstices: 1 = Shallow 2 = Medium Deep 3 = Deep | 2 | 2 |
| 8. RIND TEXTURE: | | |
| Texture: 1 = Soft 2 = Firm 3 = Hard | 2 | 2 |
| Thickness at Medial in mm | 5.35 | 4.39 |
| 9. RIND COLOR: | 01 = White 02 = Cream 03 = Buff 04 = Yellow 05 = Gold 06 = Green 07 = Orange 08 = Bronze 09 = Brown 10 = Gray 11 = Black 12 = Other (Specify)_____ | |
| Color Chart Name | RHS | RHS |
| Rind Color At Edible Maturity | | |
| Primary Color/ | 04/05 | 05/07 |
| Color Chart Value | 17C (Yellow Orange) | 21A (Yellow Orange) |
| Mottling Color/ | N.A. | N.A. |
| Color Chart Value | | |
| Net Color/ | 02/03 | 02/03 |
| Color Chart Value | 159A (Orange White) | 158A (Yellow White) |
| Furrow (Suture)/ | N.A. | 06 |
| Color Chart Value | | N137A (Green) |
| Rind Color At Full Maturity | | |
| Primary Color/ | 05/07 | 08 |
| Color Chart Value | 163B (Greyed Orange) | 22A (Yellow Orange) |
| Mottling Color/ | N.A. | N.A. |
| Color Chart Value | | |
| Net Color/ | 07/02 | 07/02 |
| Color Chart Value | 164D (Orange White) | 159B (Orange White) |
| Furrow (Suture)/ | N.A. | 06 |
| Color Chart Value | | 136A (Green) |
| 10. FLESH (At Edible Maturity): | 01 = White 02 = Cream 03 = Yellow 04 = Green 05 = Orange 06 = Salmon 07 = Pink 08 = Other (Specify) Magenta_____ | |
| Color Chart Name | RHS | RHS |
| Color Near Cavity/ | 08 | 05 |
| Color Chart Value | 32D (Orange Red) | 24B (Orange) |
| Color in Center/ | 08 | 05 |
| Color Chart Value | 32C (Orange Red) | 24A (Orange) |
| Color Near Rind/ | 08 | 05 |
| Color Chart Value | 32C (Orange Red) | 24A (Orange) |
| Refractometer % Soluable Solids (Center of Flesh) | 12.73 | 12.02 |
| Aroma: 1 = Absent 2 = Faint 3 = Strong | 1 | 2 |
| Flavor: 1 = Mild 2 = Somewhat Spicy 3 = Very Spicy | 1 | 1 |
| 11. SEED CAVITY: | | |
| Length in mm | 110.48 | 105.53 |
| Width in mm | 53.68 | 60.79 |
| Shape in X-Section: 1 = Circular 2 = Triangular | 1 | 1 |
| 12. SEEDS: | | |
| No. Seeds per Fruit | 664 | 561 |
| gm per 1,000 Seeds | 38 | 30 |

TABLE 1-continued

| USDA Descriptor | Application Variety NUN 26191 MEM | Comparison Variety Sun Delicious |
|---|---|---|
| 13. DISEASE RESISTANCE: | 0 = not tested; 1 = susceptible, 2 = resistant | |
| Bacterial Wilt | 1 | 1 |
| Root Rot | 1 | 1 |
| Crown Blight | 1 | 1 |
| Melon Rust | 0 | 0 |
| Powdery Mildew | 2 | 2 |
| Verticillum Wilt | 0 | 0 |
| Sulphur Burn | 2 | 2 |
| Scab | 0 | 0 |
| Watermelon Mosaic | 0 | 0 |
| Downy Mildew | 2 | 2 |
| *Fusarium* Wilt | 1 | 1 |
| Root Knot (Nematode) | 2 | 2 |
| Anthracnose | 1 | 1 |
| Cucumber Mosiac | 0 | 0 |
| Squash Mosaic | 0 | 0 |
| Other (specify) _____ | 0 | 0 |
| 14. INSECT RESISTANCE: | 0 = not tested; 1 = susceptible, 2 = resistant | |
| Aphid | 1 | 1 |
| Pickle Worm | 0 | 0 |
| Darkling Ground Beetle | 0 | 0 |
| Banded Cucumber Beetle | 0 | 0 |
| Mite | 0 | 0 |
| Western Spotted Cucumber Beetle | 0 | 0 |
| Melon Leafhopper | 0 | 0 |
| Melon Worm | 0 | 0 |
| Western Striped Cucumber Beetle | 0 | 0 |
| Melon Leafminer | 0 | 0 |
| Other (Specify) _____ | 0 | 0 |

These are typical values. Values may vary due to environment. Other values that are substantially equivalent are also within the scope of the invention. N.A.=not applicable; n.r.=not recorded.

The invention claimed is:

1. A seed of melon variety NUN 26191 MEM, wherein a representative sample of said seed has been deposited under Accession Number NCIMB 42420.

2. A plant produced by growing the seed of claim 1.

3. A plant part produced from the plant of claim 2.

4. A method of producing a melon plant, comprising crossing the plant of claim 2 with a second melon plant one or more times, and selecting progeny from said crossing.

5. A method of producing a melon plant, comprising selfing the plant of claim 2 one or more times, and selecting progeny from said selfing.

6. Progeny of the plant of claim 2 wherein said progeny have all the physiological and morphological characteristics of melon variety NUN 26191 MEM when grown under the same environmental conditions.

7. A method of producing plants, or a part thereof, of variety NUN 26191 MEM comprising vegetative propagation of the plant of claim 2 or a regenerable part of progeny thereof.

8. The method of claim 7, wherein said vegetative propagation comprises regenerating a whole plant from a part of variety NUN 26191 MEM.

9. The method of claim 8, wherein said part is a cutting, a cell culture or a tissue culture.

10. A vegetative propagated plant of variety NUN 26191 MEM of claim 2, or a part thereof, having all the morphological and physiological characteristics of NUN 26191 MEM when grown under the same environmental conditions, wherein a representative sample of seed of NUN 26191 MEM has been deposited under Accession Number NCIMB 42420.

11. The plant part of claim 3 or a vegetative propagated plant therefrom, wherein said plant part is selected from the group consisting of harvested fruit or parts thereof, pollen, cells, leaves or parts thereof, petioles, shoots or parts thereof, stems or parts thereof, roots or parts thereof, cuttings, flowers and parts of flowers thereof, wherein a representative sample of seed of NUN 26191 MEM has been deposited under Accession Number NCIMB 42420.

12. A food or feed product comprising the plant part of claim 11; wherein the plant part is harvested fruit or parts thereof.

13. The food or feed product of claim 12, wherein said plant part is fresh or processed.

14. A method of producing a melon plant having a desired trait, wherein the method comprises transforming the melon plant of claim 2 with a transgene that confers the desired trait, wherein the transformed plant retains all the phenotypic and morphological characteristics of variety NUN 26191 MEM and contains the desired trait, a representative sample of seed of said variety NUN 26191 MEM having been deposited under Accession Number NCIMB 42420.

15. A melon plant produced by the method of claim 14, wherein the plant comprises the desired trait and all of the physiological and morphological characteristics of NUN 26191 MEM.

16. A cell or tissue culture produced from the plant of claim 2.

17. A melon plant regenerated from the cell or tissue culture of claim 16, said plant having all the morphological and physiological characteristics of NUN 26191 MEM, wherein a representative sample having been deposited under Accession Number NCIMB 42420.

* * * * *